United States Patent [19]

Mitsuhashi et al.

[11] Patent Number: 4,803,077

[45] Date of Patent: Feb. 7, 1989

[54] PROCESS TO PREPARE SOLID PRODUCTS CONTAINING OIL-SOLUBLE SUBSTANCE

[75] Inventors: Masakazu Mitsuhashi; Shuzo Sakai; Toshio Miyake, all of Okayama, Japan

[73] Assignee: Kabushiki Kaisha Hayashibara Seibutsu Kagaku Kenkyujo, Okayama, Japan

[21] Appl. No.: 70,140

[22] Filed: Jun. 29, 1987

[30] Foreign Application Priority Data

Jul. 10, 1986 [JP] Japan .................................. 61-162657

[51] Int. Cl.$^4$ ............................................. A61K 47/00
[52] U.S. Cl. .................................... 424/439; 424/440; 424/441; 424/499; 424/502; 426/531; 426/549; 426/660; 426/658; 426/605; 426/589; 426/618; 426/557; 426/92; 426/601; 426/564; 426/654; 426/662

[58] Field of Search ............... 424/502, 451, 464, 439, 424/440, 441, 499; 426/531, 549, 660, 658, 605, 589, 618, 557, 92, 601, 564, 654, 662

[56] References Cited

U.S. PATENT DOCUMENTS 4,408,041 10/1983 Hirao et al. ........................... 424/48

Primary Examiner—Thurman K. Page
Assistant Examiner—L. R. Horne
Attorney, Agent, or Firm—Browdy and Neimark

[57] ABSTRACT

Disclosed is a novel process to prepare a solid product containing an oil-soluble substance (e.g. oil and fat, spice, flavor, vitamin, emulsifier, hormone, higher fatty acid, unsaponifiable substance and complex lipid), comprising adding to an oil-soluble liquid substance an aqueous maltose solution along with a maltose seed, and crystallizing beta-maltose hydrate to effect solidification of the mixture.

6 Claims, No Drawings

PROCESS TO PREPARE SOLID PRODUCTS CONTAINING OIL-SOLUBLE SUBSTANCE

BACKGROUND OF THE INVENTION

1. Field of the Invention

The present invention relates to a process to prepare solid products containing an oil-soluble substance, in particular, to that wherein an aqueous maltose solution is added together with a maltose seed to an oil-soluble liquid substance and then crystallized in beta-maltose hydrate form to effect solidification of the mixture.

2. Definitions and abbreviation

In the specification, percentages and parts will be expressed by weight unless specified otherwise, and dry solid basis is abbreviated as "d.s.b.".

3. Description of the prior art

Solidification using saccharides has been variously attempted to prepare oil-soluble liquid substances into solid products.

Japanese Patent Laid-Open No. 104,998/81 discloses that oil and fat are pulverable by adding water to a saccharide including glucose or lactose, heating the resultant mixture at 100°–140° C. into a porous amorphous granule, and admixing thereto an oil-soluble liquid substance such as salad oil.

This method has the drawback that it leads to a highly hygroscopic, colored product because the saccharides are exposed to a relatively high temperature.

Japanese Patent Laid-Open No. 214,845/85 discloses that lecithin is pulverable by heating a mixture of starch and lecithin together with a large amount of water to 110°–140° C., and spray-drying the resultant.

This method has the drawbacks that it deteriorates or alters lecithin because it heats lecithin with water at relatively high temperature and pressure, as well as that it consumes a relatively large amount of energy.

SUMMARY OF THE INVENTION

In order to overcome these drawbacks of conventional methods, we investigated the possibility of using maltose to convert oil-soluble liquid substances into solid products.

As the result, we found that an aqueous maltose solution, particularly, that having a maltose content of 85% or higher, d.s.b., and a moisture content lower than 20%, acts as a solidifying agent for an oil-soluble liquid substance when added together with a maltose seed and crystallized in beta-maltose hydrate form; as well as that a high-quality solid product containing the oil-soluble substance is easily obtainable by utilizing this property.

DETAILED DESCRIPTION OF THE INVENTION

The oil-soluble liquid substances as referred to in the invention are oily solvent-soluble liquids; for example, oils and fats such as soybean oil, rapeseed oil, mustard oil, sesame oil, safflower oil, cottonseed oil, palm oil, cacao butter, beef tallow, lard, chicken oil, marine oil, bone oil and hardened oil; oil-soluble flavors and spices such as citrus essential oil, flower essential oil, spice oil, peppermint oil, spearmint oil, cola nut extract and coffee extract; oil-soluble coloring agent such as beta-carotin, paprika pigment, annatto pigment and chlorophyll; oil-soluble vitamins such as liver oil, vitamin A, vitamin $B_2$ lactate, vitamin E, vitamin K and vitamin D; oil-soluble hormones such as estrogen, progesterone and androgen; unsaturated higher fatty acids such as linoleic acid, linolenic acid, arachidonic acid, eicosapentaenoic acid and docosahexaenoic acid; unsaponifiable substances such as higher alcohol, sterol and squalene; and complex lipids such as lecithin and cephalin.

The physical properties and processibility of an oil-soluble substance having a relatively high melting point, for example, hardened oil, essential oil, sterol, higher alcohol or wax, are improved first by melting it by heating or dissolving in a solvent such as alcohol, chloroform or ether; then adding an aqueous maltose solution along with a maltose seed to the resultant liquid or solution to effect solidification. In this way, the use of such oil-soluble substances can be expanded.

The present invention is advantageously applicable to oil-soluble liquid substances having a decreased moisture content, particularly, lower than 5%, more particularly, lower than 2%.

We found that an aqueous solution of a high-purity maltose having a maltose content of 85% or higher, d.s.b., and a moisture content lower than 20% is suitable for the aqueous maltose solution because it readily crystallizes in beta-maltose hydrate form even in the presence of an oil-soluble substance.

Such high-purity maltose may be a commercialized crystalline beta-maltose hydrate or that obtained by saccharifying starch in conventional manner.

As to such saccharification, Japanese Patent Publication Nos. 11,437/81 and 17,078/81 disclose that a gelatinized- or liquefied-starch is subjected to the action of beta-amylase to form maltose which is then separated from the concomitant maltodextrins; and Japanese Patent Publication Nos. 13,089/72 and 3,983/79 disclose that a gelatinized- or liquefied-starch is subjected to the actions of starch-debranching enzyme, such as pullulanase or isoamylase, and beta-amylase.

The maltose content of the obtained product can be augmented by subjecting the concomitant saccharides including maltotriose to an enzyme as disclosed, for example, in Japanese Patent Publication Nos. 28,153/81, 3,356/82 and 28,154/81, to form maltose; or separating the saccharides by the fractionation as disclosed in Japanese Patent Laid-Open No. 23,799/83 using a strongly-acidic cation exchange resin in a salt form. The fractionation is carried out by the fixed bed-, moving bed-, or simulating moving bed-method.

We found that an aqueous maltose solution, added together with a relatively small amount of a maltose seed to an oil-soluble liquid substance, for example, oil and fat, oil-soluble flavor, oil-soluble coloring agent, oil-soluble vitamin, oil-soluble emulsifier and oil-soluble hormone, crystallizes in beta-maltose hydrate form and swells about 1.2-folds or more, occasionally, about 1.5- to 4.0-folds while including a large amount of the oil-soluble substance as the conversion into crystalline beta-maltose hydrate proceeds. We confirmed that this renders anhydrous maltose an advantageously usable material for solidifying oil-soluble liquid substances.

The weight ratio of an aqueous maltose solution to an oil-soluble liquid substance is 0.5–500, desirably, 0.8–50.0.

The moisture content of the aqueous maltose solution is lower than 20%, desirably, 2.0–18.0%.

The maltose seed is usually a crystalline beta-maltose hydrate. The crystalline alpha-maltose as disclosed in Japanese Patent Laid-Open No. 35,800/86 can be used as the seed as long as its moisture content is lower than about 10%. In this case, a crystalline alpha-maltose appearing first is readily converted into crystalline beta-maltose hydrate by allowing it to stand at ambient temperature.

In either case, the amount of maltose seed is small, usually, less than 5%, desirably, about 0.5–2%.

An aqueous maltose solution and a maltose seed are added to an oil-soluble liquid substance in conventional manner during the preparation of solid product, for example, mixing, kneading, dissolving, permeating, sprinkling, applying, spraying, and injecting.

The following will illustrate the present invention much more concretely.

Crystallization of beta-maltose hydrate is attained by adding an appropriate amount of maltose seed water to either or both an oil-soluble liquid substance and an aqueous maltose solution, mixing them, and ageing the mixture by allowing it to stand at ambient temperature. In this case, the intake of the oil-soluble substance occurs homogeneously without release to give a solid product.

Alternatively, an oil-soluble liquid substance is mixed with an aqueous maltose solution, and the resultant is seeded and aged similarly as above.

In either case, a surface active agent may be used.

If necessary, one or more of flavor, coloring agent, seasoning, surface active agent, antioxidant, stabilizer and filler may be used in combination.

The stabilizer and filler include water-soluble polymers, for example, solubilized starch, dextrin, cyclodextrin, pullulan, elsinan, dextran, xanthan gum, gum arabic, locust bean gum, guar gum, tragacanth gum, tarmalind gum, carboxymethyl cellulose, hydroxyethyl cellulose, pectin, agar, gelatin, albumin and casein.

The present invention is variously practiced in the preparation of solid products containing an oil-soluble substance, particularly, those in powder. For example, an aqueous maltose solution and a maltose seed are added to an oil-soluble liquid substance as described above, and the mixture is placed in a tray, and solidified, for example, into block while accelerating the crystallization of beta-maltose hydrate by allowing the mixture to stand at about 10°–60° C. for about 0.1–10 days. The block is pulverized by cutting and scraping, followed by drying and/or sieving, if necessary. Powder and granule are directly preparable with spray-drying. For example, an oil-soluble liquid substance is mixed with an aqueous maltose solution and a seed, and the mixture wherein crystallization is initiated is granulated by spraying. The resultant granule is aged while accelerating the crystallization of beta-maltose hydrate at about 30°–60° C. for about 1–24 hours. Thus, a stable powder is obtained.

The pulverulent product thus obtained is usable alone or, if necessary, in combination with one or more of filler, vehicle, binder and stabilizer. The product may be shaped into granule, tablet, capsule, rod, plate or cube, prior to its use.

The product is a high-quality, non-hygroscopic and stable solid free of browning, coloring, volatilization of flavors, alteration or deterioration of effective ingredients because its preparation used no vigorous heating step.

The product is extensively usable, for example, as or in flavoring agents, coloring agents, emulsifying agents, food products, pharmaceuticals, cosmetics, toiletries, and intermediates thereof, dependently on the properties of the oil-soluble substance.

Several embodiments and superior effects of the present invention will hereinafter be described.

EXAMPLE 1

Powder containing salad oil

One-hundred and fifty parts of soybean salad oil was mixed with one part of lecithin, 200 parts of an aqueous maltose solution, maltose content of 92.5%, d.s.b., moisture content of 12%, and a beta-maltose hydrate seed, and the mixture was crystallized, placed in a tray, solidified and aged while accelerating the crystallization of beta-maltose hydrate by allowing it to stand at ambient temperature for two days.

The resultant block was fed to a pulverizer, and the resultant was dehydrated by ventilation, and sieved to obtain a high-quality powder containing salad oil.

The product was advantageously usable for preparing confectioneries such as premix, frozen dessert, cake and candy; foods such as mayonnaise, dressing, potage soup, stew and "chahan (mixed fried rice)"; medicines for promoting nutrition such as intubation feeding; and feeds.

EXAMPLE 2

Granule containing "rayu (a hot oil made from sesame oil and cayenne pepper)"

Fifty parts of rayu was mixed with 100 parts of an aqueous maltose solution, maltose content of 88.5%, d.s.b., moisture content of 13%, and a beta-maltose hydrate seed, and the mixture was crystallized, solidified, aged, pulverized similarly as in Example 1, and fed to a granulator to obtain a granule excellent in taste and flavor.

The product is advantageously usable as a seasoning for Chinese dishes such as "ramen (Chinese noodle)", instant ramen, "gyoza (a fried dumpling stuffed with minced pork)", and "wantan (a Chinese flour dumpling with pork)".

EXAMPLE 3

Powder containing bone oil

Two hundred parts of an aqueous maltose solution, maltose content of 94.4%, d.s.b., moisture content of 5.0%, was seeded by the addition of a crystalline alpha-maltose, and the resultant mixture was mixed with 150 parts of bone oil. The resultant was solidified, aged by allowing it to stand at ambient temperature for two days, fed to a pulverizer, and dried by one-day ventilation at ambient temperature.

The product is advantageously usable as or a health-promoting agent, tonic, cosmetic and feed intact or after shaped into granule or tablet.

EXAMPLE 4

Powder containing shortening

One hundred parts of shortening was mixed with one part of lecithin, 200 parts of an aqueous maltose solution as used in Example 3, and a beta-maltose hydrate seed, and the mixture was crystallized and sprayed downwards from the top of a spray-drying tower through a nozzle with a high pressure pump in a 50° C. air stream. The resultant powder was collected at the bottom of the tower, placed in an ageing tower, and aged at 30° C. overnight to obtain a high-quality powder containing shortening.

Similarly as the product in Example 1, the product is advantageously usable in confectioneries, cooked products, medicines for promoting nutrition, and feeds.

EXAMPLE 5

Powder containing lecithin

One hundred and thirty parts of an aqueous maltose solution, maltose content of 92.5%, d.s.b., moisture content of 6.0%, was seeded by the addition of a crystalline alpha-maltose and then mixed with 70 parts of egg lecithin, and the mixture was solidified, aged and pulverized similarly as in Example 3.

The product having a strong emulsifying power is advantageously usable as or in emulsifying agent for oils and fats; foaming agent for confectioneries such as sponge cake, cookie and biscuit; emulsion stabilizer; agent to improve the quality of oily food products, noodle, vermicelli and creams; and cosmetic.

EXAMPLE 6

Powder containing eicosapentaenoic acid

Four parts of gamma-cyclodextrin powder was dissolved in 100 parts of an aqueous maltose solution, maltose content of 96.5%, d.s.b., moisture content of 18%, and the solution was mixed with 4 parts of eicosapentaenoic triglyceride and a beta-maltose hydrate seed. The mixture was crystallized, solidified, aged, pulverized and dehydrated by the method in Example 3.

The eicosapentaenoic acid in the product is very stable because it forms an inclusion compound together with cyclodextrins.

The product is advantageously usable in health foods and pharmaceuticals wherein eicosapentaenoic acid provides anticholesteremic- and arteriosclerosis preventing-activities.

As obvious from the above, the present invention relates to a process to prepare solid products containing an oil-soluble substance, particularly, to that wherein an aqueous maltose solution, added along with a maltose seed to an oil-soluble liquid substance, for example, oil and fat, oil-soluble flavor, oil-soluble coloring agent, and oil-soluble emulsifier, is crystallized in beta-maltose hydrate form while allowing it to take in a relatively large amount of the oil-soluble substance.

Since the process contains no vigorous processing step, it causes no deterioration or alteration of the taste, flavor and effective ingredient(s) of an oil-soluble liquid substance. Thus, a high-quality solid product is easily obtainable.

The product thus obtained is advantageously usable in flavoring agents, coloring agents, emulsifying agents, cosmetics, toiletries, and intermediates thereof.

While the preferred forms of the present invention have been described, it is to be understood that modifications will be apparent to those skilled in the art without departing from the spirit of the invention.

The scope of the invention, therefore, is to be determined solely by the following claims.

We claim:

1. A process to prepare a solid product containing an edible oil-soluble substance, comprising:
   adding an aqueous maltose solution along with a maltose seed to an oil-soluble liquid substance; and
   crystallizing beta-maltose hydrate in the mixture to effect solidification.

2. The process of claim 1, wherein said edible oil-soluble liquid substance contains a surface active agent.

3. The process of claim 1, wherein said aqueous maltose solution has a maltose content of 85% by weight or higher based on the dry solid and a moisture content lower than 20% by weight.

4. The process of claim 1, wherein the weight ratio of the edible oil-soluble substance to maltose is in the range of about 1.0-0.5-1.0:500.

5. The process of claim 1, wherein said solid product is in the form of powder, granule, tablet, capsule, rod or plate.

6. The process of claim 1, wherein said solid product is a member selected from the group consisting of flavoring agent, coloring agent, emulsifying agent, food product, pharmaceutical, cosmetic and, toiletries.

* * * * *